United States Patent [19]

Mueller et al.

[11] 3,960,912
[45] June 1, 1976

[54] PROCESS FOR THE PREPARATION OF TRIALKYL ALUMINUM COMPOUNDS

[75] Inventors: Karl Heinz Mueller, Werne; Hans-Juergen Hubert, Hamm, both of Germany

[73] Assignee: Schering Aktiengesellschaft, Berlin and Bergkamen, Germany

[22] Filed: Dec. 11, 1974

[21] Appl. No.: 531,738

[30] Foreign Application Priority Data
Dec. 13, 1973   Germany............................ 2361988

[52] U.S. Cl............................................. 260/448 A
[51] Int. Cl.² ........................................... C07F 5/06
[58] Field of Search ................................ 260/448 A

[56] References Cited
UNITED STATES PATENTS

| | | | |
|---|---|---|---|
| 3,207,770 | 9/1965 | Liegler et al.................. | 260/448 A |
| 3,373,179 | 3/1968 | Lewis............................. | 260/448 A |
| 3,388,142 | 6/1968 | Cameron et al. .............. | 260/448 A |
| 3,423,444 | 1/1969 | Atwood ......................... | 260/448 A |
| 3,445,494 | 5/1969 | Acciarri......................... | 260/448 A |

OTHER PUBLICATIONS
Mole et al., Organoaluminum Compounds, Elsevier Publ. Co., N. Y., pp. 62–67 and 79–84 (1972).

*Primary Examiner*—Helen M. S. Sneed
*Attorney, Agent, or Firm*—Curtis, Morris & Safford

[57] ABSTRACT

A process for the preparation of a trialkyl aluminum compound of the formula $(RCH_2CH_2)_3Al$, wherein R is hydrogen or alkyl having 1 to 18 carbon atoms, which process comprises (A) reacting aluminum, hydrogen, and a mixture of said trialkyl aluminum compound and the corresponding dialkyl aluminum hydride in a first stage to form a first product which is said dialkyl aluminum hydride alone or in admixture with unreacted trialkyl aluminum compound; (B) reacting said first product with an olefin of the formula $RCH=CH_2$, where R has its earlier meaning, in a second stage to form a second product which is a mixture of said trialkyl aluminum compound and the corresponding dialkyl aluminum hydride; and (C) recycling a portion of this second product from said second stage to said first stage and reacting the remainder of said second product with further olefin of the formula $RCH=CH_2$ in a third stage to form said trialkyl aluminum compound.

2 Claims, 1 Drawing Figure

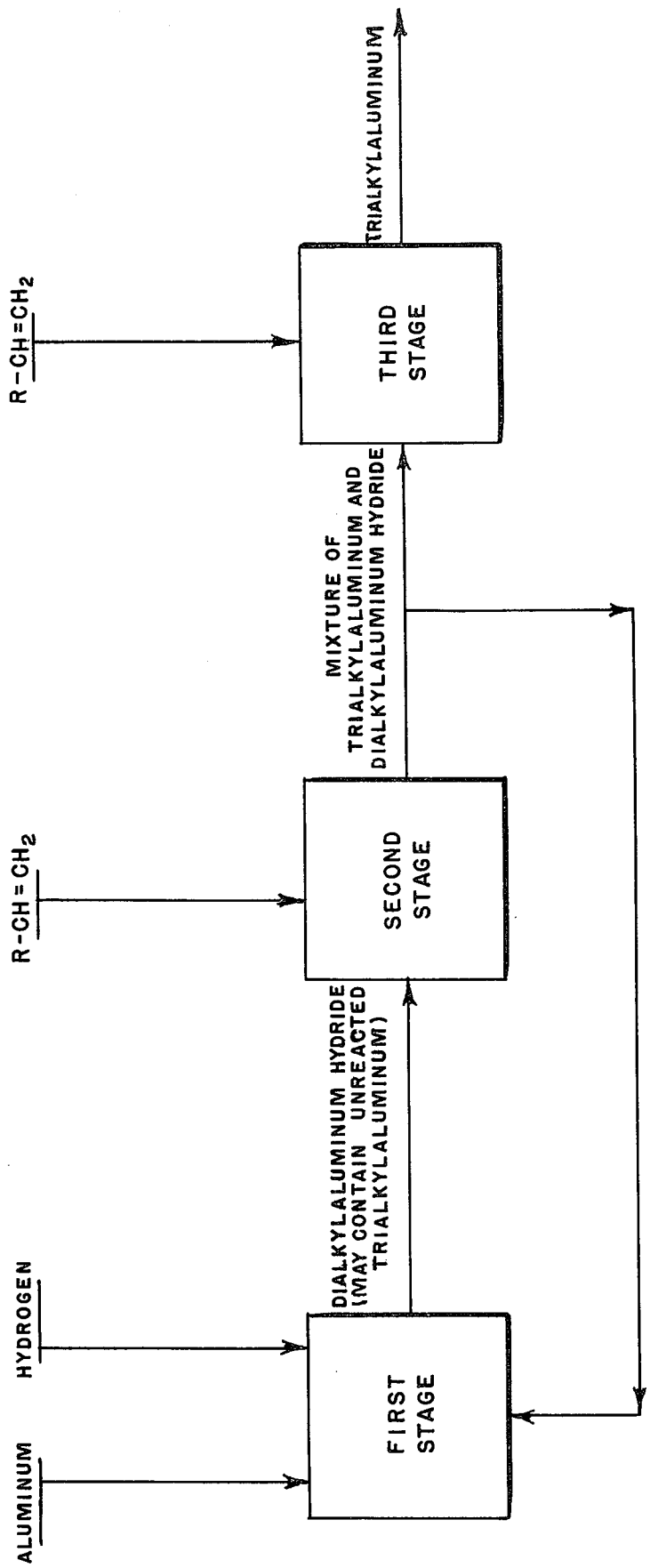

PROCESS FOR THE PREPARATION OF TRIALKYL ALUMINUM COMPOUNDS

The present invention relates to a method for preparing trialkyl aluminum compounds having alkyl groups which are unsubstituted in the β-position, particularly n-alkyl groups, such as triethyl aluminum, tri-n-propyl aluminum, tri-n-butyl aluminum, and tri-n-octyl aluminum, for example.

The compounds are prepared from aluminum, hydrogen and olefins of the general formula $CH_2 = CH-R$, wherein R is hydrogen or an alkyl group having 1 to 18 carbon atoms, preferably 1 to 8 carbon atoms.

According to the prior art, the preparation of such trialkyl aluminum compounds from aluminum, hydrogen, and olefins take place, as does the aforementioned improved process of the present invention, according to the following reaction scheme:

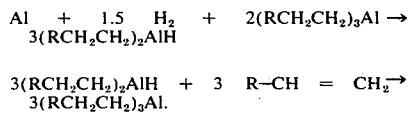

$$Al + 1.5\ H_2 + 2(RCH_2CH_2)_3Al \rightarrow 3(RCH_2CH_2)_2AlH$$

$$3(RCH_2CH_2)_2AlH + 3\ R-CH = CH_2 \rightarrow 3(RCH_2CH_2)_3Al.$$

The process according to the state of the art is described in a number of patents, for example in German Pat. Nos. 961,537; 1,031,792; 1,086,699; 1,118,782; 1,158,517; 1,167,837; and 2,058,487.

In the simplest embodiment of the prior art process, the two above-identified reactions occur concurrently in a reaction volume, a process which requires the concurrent presence of all materials participating in the reaction. Such a one-step process can be controlled and also gives good yields of trialkyl compounds. However, it is difficult to direct the process in such a manner that trialkyl aluminum compounds of high purity are obtained, particularly in the case of the preparation of triethyl aluminum. Namely, ethylene tends to a particularly high degree to add to trialkyl aluminum, which leads to the formation of higher trialkyl aluminum compounds which can be separated practically only by distillation.

In a different embodiment of the prior art process, trialkyl aluminum is reacted with aluminum and hydrogen in a first step with formation of dialkyl aluminum hydrides. The reaction of the dialkyl aluminum hydrides and olefins with formation of trialkyl aluminum first takes place in a second step of such a process. According to this embodiment, trialkyl aluminum compounds of high purity are more easily prepared. However, for many uses, the purity obtainable in this way is not sufficient and one is forced to reduce the content of higher trialkyl aluminum compounds by way of a supplemental purification operation, for example a distillation, which is time consuming and expensive.

According to the present invention, a process for the preparation of trialkyl aluminum compounds of the general formula $(RCH_2CH_2)_3Al$, wherein R is hydrogen or an alkyl group having 1 to 18 carbon atoms, has been found, whereby a reaction of, on the one hand, aluminum and aluminum trialkyl and hydrogen at temperatures of 80°C. – 180°C. and at pressures of 50 – 250 atmospheres is combined, on the other hand, with a reaction of dialkyl aluminum hydrides with olefins of the general formula $R-CH = CH_2$, wherein R is hydrogen or an alkyl group having 1 to 18 carbon atoms, at temperatures of 60°C. – 140°C. and at pressures of 1 to less than 20 atmospheres especially from 1 to 10 atmospheres.

In the process, 1. a mixture of trialkyl aluminum and the corresponding dialkyl aluminum hydride having a content of dialkyl aluminum hydride of 3 – 50 mol percent is partially or completely converted in a first stage to the dialkyl aluminum hydride; and
2. the dialkyl aluminum hydride, which may still contain unreacted trialkyl aluminum, is partially reacted with an olefin of the aforementioned formula in a second stage to form a mixture of trialkyl aluminum and dialkyl aluminum hydride having a content of dialkyl aluminum hydride of 3 – 50 mol percent and a portion of this reaction mixture is recirculated to the first stage; and
3. the residue of the reaction mixture from the second stage is reacted with olefin of the aforementioned formula in a third stage to form trialkyl aluminum.

The improvement obtained with the aid of the 3-step process of the present invention, in comparison with the prior art, lies particularly in that trialkyl aluminum compounds of very high purity can be easily obtained. No distillation of the trialkyl aluminum compounds prepared according to the present invention is necessary for separating higher trialkyl aluminum compounds. Also, according to the 3-stage process of the invention, it is very easy to prepare very pure trialkyl aluminum compounds with a very small content of dialkyl aluminum hydride. Such a result is particularly necessary if the trialkyl aluminum compounds, such as triethyl aluminum, are used for preparing mixed catalysts for the polymerization of olefins or are used for the preparation of other organic aluminum compounds, such as diethyl aluminum chloride, which in turn can be used for preparing catalysts for olefin polymerization.

A further advantage of the process of the present invention is that it can be carried out very easily in a continuous fashion. According to the flow chart shown in the accompanying Figure, activated aluminum, suitably activated aluminum powder, is continually introduced into the reactor of the first stage with hydrogen and with a mixture, recirculated from the second stage, of trialkyl aluminum and dialkyl aluminum hydride. The mixture which is recirculated from the second to the first stage contains from 3 – 50 mol percent of dialkyl aluminum hydride. In the reactor of the first stage, the reaction proceeds at temperatures of 80°C. – 180°C. and at hydrogen pressures from 50 – 250 atmospheres. The reaction is weakly exothermic. Suitable reactors for use in the first stage are known in the art. The dialkyl aluminum hydride which is continuously removed from the reactor and which may contain still-unreacted trialkyl aluminum is depressurized and unreacted aluminum is suitably separated. The degree of the reaction should be as high as possible. It is sufficient, however, if the content of the reaction mixture in dialkyl aluminum hydride is between 60 and 90 mol percent.

The reaction product of the first stage is subsequently introduced, together with an olefin of the general formula $CH_2 = CH-R$, into a reactor suitable for the reaction of the second stage. This reactor has a temperature of 60°C. – 140°C. For olefins in the gaseous phase, a constant pressure from 1 to less than 20 atmospheres is maintained. The dwell time is so measured that the exit product still contains dialkyl aluminum hydride in an amount from 3 to 50 mol percent. The reaction is strongly exothermic. Reactors suitable for the addition of olefins to dialkyl aluminum hydride are also known in the art.

By passage through the first and second reaction stages, the mixture of trialkyl aluminum and dialkyl aluminum hydride is increased in amount. An amount corresponding to that amount additionally formed is continually fed, together with further olefin, into a reactor in a third stage. The remaining residual mixture of trialkyl aluminum and dialkyl aluminum hydride is recirculated to the first stage. The portion of the mixture of trialkyl aluminum and dialkyl aluminum hydride which is reintroduced into the first stage suitably is between 70 and 85 percent of the reaction product from the second stage.

In the reactor of the third stage, the reaction forming trialkyl aluminum compound is carried out. The reaction temperature is between 60°C. – 140°C. When olefins in the gaseous phase are employed, a constant pressure from 1 to less than 20 atmospheres is maintained. The reaction is exothermic. The final product is continuously removed from the third reactor and degassed.

The reactions of the second and third stages can also take place in one, or in more than two, reactors. When a single reactor is used, the mixture of trialkyl aluminum and dialkyl aluminum hydride is removed from a particular portion of the reactor and re-circulated to the first stage. The reactor should be so arranged that no back mixing can ococur. This is particularly true for the reactor or reactor portion in which the third stage of the reaction is carried out. In all reactions and operations, care should be taken that the aluminum alkyl compounds cannot come in contact with air or water.

A better understanding of the present invention and its many advantages will be had by referring to the following specific examples, given by way of illustration.

EXAMPLE 1

50 liters per hour of triethyl aluminum having a diethyl aluminum hydride content of 30 mol percent were continuously introduced into the first stage of a continuously operating pilot reactor, operating according to the flow sheet of the accompanying Figure, together with 3.4 kg of aluminum powder having a content of about 99.5 percent aluminum and 0.2 percent titanium. The aluminum powder was priorly activated by milling in a ball mill in the presence of aluminum triethyl. Hydrogen was continuously circulated, a pressure of 150 atmospheres being maintained by the addition of fresh hydrogen. The cylindrically shaped sieve plate reactor employed had a production volume of 44 liters. The reaction temperature was 125°C. This constant temperature was assured by the use of a controllable temperature arrangement. The exiting reaction product was depressurized in an elongated separator and freed from residual aluminum by filtration. It had a diethyl aluminum hydride content of 84 mol percent.

50 liters of the filtered reaction product of the first stage were introduced hourly into a cylindrically shaped sieve plate reactor in the second stage (production volume, 15 liters). Ethylene was circulated, the pressure of atmospheres being maintained by the addition of fresh ethylene. The reaction temperature was 100°C. The heat of the reaction was dissipated using a controllable cooling system. The exiting product was depressurized. It had a residual content of diethylene aluminum hydride of 30 mol percent.

80 percent of the reaction product of the second stage was re-circulated into the first stage; 20 percent was introduced into the third stage, which was put into operation after a sufficient shock of starting material for the third stage had accumulated. 24 liters per hour of the reaction product of the second stage were introduced into the cylindrically shaped sieve plate reactor of the third stage (production volume, 15 liters). Ethylene was again continuously circulated, the operating pressure of 10 atmospheres being maintained by the addition of fresh ethylene. The reaction temperature, controlled by a cooling system, was 100°C., as in the second stage. The decompressed end product, after the total system had reached a stationary state, was triethyl aluminum. On hydrolysis, the gaseous prodcuts indicated the following product composition:

95.9 percent by weight of triethyl aluminum,
0.2 percent by weight of diethyl aluminum hydride, and
3.9 percent by weight of tributyl aluminum.

COMPARISON EXAMPLE

In the continuously operating pilot apparatus described in Example 1, the preparation of triethyl aluminum was carried out in an analogous fashion in a two-step process, eliminating the third stage.

The hourly input in the first stage was 40 liters of triethyl aluminum containing 0.3 mol percent of diethyl aluminum hydride, 3.8 kg of activated aluminum having a content of about 99.5 percent aluminum and 0.2 percent titanium, and circulating hydrogen. The reactor temperature was 125°C.: the reaction pressure was 150 atmospheres. The diethyl aluminum hydride content in the exit product was 84 mol percent.

19 liters of filtered exit product from the first stage and ethylene were circulated per hour in the second stage. The reactor temperature was 100°C.; the reaction pressure was 10 atmospheres.

72 percent of the reaction product was recirculated to the first stage and 28 percent was withdrawn as the final product.

The composition of the final product, after steady state conditions were reached, was determined from the hydrolysis gases to be:

88.3 weight percent of triethyl aluminum,
0.2 weight percent of diethyl aluminum hydride, and
11.5 weight percent of tributyl aluminum.

EXAMPLE 2

Reactions were carried out as described in Example 1 in a continuously operating three-stage pilot apparatus.

40 liters of triethyl aluminum with a diethyl aluminum hydride content of 10 mol percent and 3.4 kg of activated aluminum powder having a content of about 99.5 percent aluminum and 0.2 percent titanium were introduced per hour into the first stage. Hydrogen was circulated, with the pressure thereof being maintained by the addition of fresh hydrogen.

The reactor temperature was 125°C., the reactor pressure was 150 atmospheres. The diethyl aluminum hydride content in the product exiting from the reactor was 82 mol percent.

50 liters of the filtered reaction product of the first stage were introduced per hour into the second stage. Ethylene was circulated and the pressure maintained by the addition of fresh ethylene. The reactor temperature was 100°C., the reactor pressure was 8 atmospheres. The diethyl aluminum hydride content in the product exiting from the reactor was 10 mol percent. 75 percent of the reaction product was recirculated to the first stage, while 25 percent was introduced into the third stage.

40 liters of reaction product of the second stage were introduced per hour into the third stage. The ethylene was circulated, its pressure maintained by the introduction of fresh ethylene. The reactor temperature was 100°C.; the reactor pressure was 6 atmospheres. The composition of the decompressed end product, after steady state conditions had been reached, was determined from the hydrolysis gases as follows:

94.4 weight percent of triethyl aluminum,
1.4 weight percent of diethyl aluminum hydride, and
4.2 weight percent of tributyl aluminum.

EXAMPLE 3

The reactions of this Example were carried out continuously in the three-stage pilot apparatus described in Example 1.

30 liters of tri-n-butyl aluminum having a di-n-butyl aluminum hydride content of 6 mol percent and 1.7 kg of activated aluminum powder having a content of about 99.5 percent aluminum and 0.015 percent titanium were introduced hourly into the first stage. Hydrogen was cycled and the pressure maintained constant by the addition of fresh hydrogen. The reactor temperature was 130°C.: the reactor pressure was 135 atmospheres. The di-n-butyl aluminum hydride content in the product leaving the first stage was 82 mol percent.

The hourly input into the second stage was 50 liters of filtered reaction product from the first stage. n-butene-1 was circulated, with the pressure maintained constant by the addition of fresh n-butene-1. The reactor temperature was 100°C.; the reactor pressure was 6 atmospheres. The di-n-butyl aluminum hydride content in the product leaving the second stage was 6 mol percent. 74 percent of the de-gassed reaction product was re-circulated back to the first stage and 26 percent was introduced into the third stage.

The hourly input into the third stage was 50 liters of reaction product from the second stage. n-butene-1 was recycled, with its pressure kept constant by the addition of fresh n-butene-1. The reactor temperature was 100°C.; the reactor pressure was 5 atmospheres. The composition of the de-gassed and final product after a steady state was reached was calculated as follows from hydrolysis gases:

97.9 percent by weight of tri-n-butyl aluminum,
0.6 percent by weight of di-n-butyl aluminum hydride, and
1.5 percent by weight of tri-2-ethylhexyl aluminum.

EXAMPLE 4

The reaction was carried out in the continuously operating pilot reactor described in Example 1 operating in three stages.

The hourly input in the first stage was 15 liters of tri-n-octyl aluminum having a di-n-octyl aluminum hydride content of 11 mol percent and 0.44 kg of activated aluminum having a content of about 99.5 percent aluminum and 0.015 percent titanium. Hydrogen was cycled, its pressure being maintained constant by the introduction of fresh hydrogen. The temperature in the reactor in the first stage was 125°C.; the reactor pressure was 130 atmospheres. The product leaving the first stage had a di-n-octyl aluminum hydride content of 80 mol percent.

20 liters of the filtered reaction product from first stage and 6.3 liters of n-octene-1 were introduced per hour into the second stage. The reactor temperature here was 90°C.; the reactor pressure was 1 atmosphere. The product leaving the second stage had a di-n-octyl aluminum hydride content of 11 mol percent. 76 percent of this reaction product was recycled to the first stage, while 24 percent was introduced into the third stage.

The hourly input in the third stage was 20 liters of reaction product from the second stage and 1.4 liters of n-octene-1. The reactor temperature in the third stage was 95°C.; the reactor pressure was 1 atmosphere. The composition of the de-gassed reaction product after a steady state had been reached was determined from hydrolysis gases as:

98.2 percent by weight of tri-n-octyl aluminum,
0.8 percent by weight of di-n-octyl aluminum hydride, and
1.0 percent by weight of tri-2-hexyldecyl aluminum.

What is claimed is:

1. In a process for the preparation of a trialkyl aluminum compound of the formula $(R-CH_2-CH_2)_3 Al$, wherein R is hydrogen or alkyl having up to 18 carbon atoms, by reacting aluminum and hydrogen, in the presence of said trialkyl aluminum compound, in a first stage at a temperature from 80°C. to 180°C. and at a pressure from 50 to 250 atmospheres to form the corresponding dialkyl aluminum hydride, decompressing the dialkyl aluminum hydride product and reacting it in a second stage with an olefin of the formula $R-CH=CH_2$ at a temperature from 60°C. to 140°C. and at a pressure from 1 to 20 atmospheres to form said trialkyl aluminum compound, and recycling a portion of said trialkyl aluminum compound to said first stage, the improvement wherein
   1. said aluminum and hydrogen are reacted in said first stage in the presence of a mixture of said trialkyl aluminum and of the corresponding dialkyl aluminum hydride, which mixture contains from 3 to 50 mol percent of said dialkyl aluminum hydride, to form a reaction product which is said dialkyl aluminum hydride alone or in admixture with unreacted trialkyl aluminum;
   2. this product from the first stage is partially reacted in said second stage with an olefin of the formula $R-CH=CH_2$ to form a mixture of trialkyl aluminum hydride and the corresponding dialkyl aluminum hydride, which mixture contains from 3 to 50 mol percent of dialkyl aluminum hydride;
   3. a portion of the reaction product from this second stage is recycled to said first stage; and
   4. the remainder of the reaction product from this second stage is reacted, also at a temperature from 60°C. to 140°C. and at a pressure from 1 to 20 atmospheres, in a third stage with further olefin of the formula $R-CH=CH_2$ to form said trialkyl aluminum, whereby a highly pure trialkyl aluminum product is obtained.

2. A process as in claim 1 wherein the pressure in said second stage is from 1 to 10 atmospheres.

* * * * *